US008940549B2

(12) United States Patent
Kondou et al.

(10) Patent No.: US 8,940,549 B2
(45) Date of Patent: Jan. 27, 2015

(54) IMMUNOASSAY REAGENT FOR KL-6 ASSAY

(75) Inventors: Junichi Kondou, Ryugasaki (JP); Mitsuaki Yamamoto, Ryugasaki (JP); Chie Kaneko, Ryugasaki (JP)

(73) Assignees: Sekisui Medical Co., Ltd., Tokyo (JP); Eidia Co., Ltd., Tokyo (JP)

( * ) Notice: Subject to any disclaimer, the term of this patent is extended or adjusted under 35 U.S.C. 154(b) by 570 days.

(21) Appl. No.: 13/258,468

(22) PCT Filed: Jun. 30, 2010

(86) PCT No.: PCT/JP2010/061109
§ 371 (c)(1),
(2), (4) Date: Oct. 18, 2011

(87) PCT Pub. No.: WO2011/001999
PCT Pub. Date: Jan. 6, 2011

(65) Prior Publication Data

US 2012/0040476 A1 Feb. 16, 2012

(30) Foreign Application Priority Data

Jun. 30, 2009 (JP) ................................ 2009-155075

(51) Int. Cl.
*G01N 33/546* (2006.01)
*G01N 33/68* (2006.01)

(52) U.S. Cl.
CPC .... *G01N 33/6884* (2013.01); *G01N 2333/4725* (2013.01); *Y10S 436/805* (2013.01); *Y10S 436/808* (2013.01); *Y10S 436/815* (2013.01)
USPC ........... 436/534; 436/518; 436/531; 436/536; 436/538; 436/164; 436/805; 436/808; 436/815

(58) Field of Classification Search
CPC .......... G01N 33/537; G01N 33/54313; G01N 33/546; G01N 2400/00
USPC ......... 436/518, 531, 534, 536, 538, 164, 805, 436/808, 815
See application file for complete search history.

(56) References Cited

U.S. PATENT DOCUMENTS

2005/0084846 A1 4/2005 Okamoto et al.

FOREIGN PATENT DOCUMENTS

| | | | |
|---|---|---|---|
| JP | 7-31207 | B2 | 12/1987 |
| JP | 2005-121441 | A | 5/2005 |

OTHER PUBLICATIONS

Arase et al., "Usefulness of serum KL-6 for early diagnosis of idiopathic pulmonary fibrosis in patients with hepatitis C virus," Hepatology Research (2003), vol. 27, pp. 89-94.
Bernard, A. and R. Lauwerys, "Turbidimetric Latex Immunoassay for Serum Ferritin," Journal of Immunological Methods (1984), vol. 71, pp. 141-147.
Cambiaso, C. L. and J. N. Limet, "Latex agglutination assay for human anti-*Brucella* IgM antibodies," Journal of Immunological Methods (1989), vol. 122, pp. 169-175.
Extended European Search Report issued Mar. 22, 2013, in European Patent Application No. 10794167.6.
Passelecq et al., "Latex immunoassay of serum α-fetoprotein using polyethylene glycol pretreatment," Journal of Immunological Methods (1988), vol. 109, pp. 69-74.
International Search Report, dated Sep. 21, 2010 in PCT/JP2010/061109.
Ohshimo et al., "KL-6, a human MUC1 mucin, promotes proliferation and survival of lung fibroblasts", Biochemical and Biophysical Research Communications, 2005, vol. 338, pp. 1845-1852.
International Preliminary Report on Patentability mailed Feb. 23, 2012, in PCT International Patent Application No. PCT/JP2010/061109.

*Primary Examiner* — Chris L Chin
(74) *Attorney, Agent, or Firm* — Birch, Stewart, Kolasch & Birch, LLP

(57) ABSTRACT

The present invention aims to provide an assay reagent and an assay for accurately measuring KL-6, in particular, an assay reagent and an assay for accurately measuring KL-6 in samples containing a rheumatoid factor and/or a nonspecific substance other than the rheumatoid factor. KL-6 in samples that contain a rheumatoid factor and/or a nonspecific substance other than the rheumatoid factor can be accurately measured using an immunoassay reagent comprising a solution at a pH of 4.0 to 5.5 containing a rheumatoid factor interference inhibitor and a solution of an insoluble carrier on which anti-KL-6 antibodies are immobilized.

7 Claims, No Drawings

IMMUNOASSAY REAGENT FOR KL-6 ASSAY

TECHNICAL FIELD

The technical field of this invention concerns an assay reagent and an assay for KL-6 measurement in a sample. Furthermore, the technical field of the present invention concerns an immunoagglutination technique, reagents, and methods to inhibit nonspecific reactions in this technique.

BACKGROUND ART

KL-6 is a sialylated carbohydrate antigen that is involved in pulmonary fibrosis (Non-Patent Literature (NPL) 1, Patent Literature (PTL) 1). KL-6 levels are measured for the diagnosis and determination of therapeutic strategies for interstitial pneumonitis because elevated KL-6 levels and their fluctuation in interstitial pneumonitis indicate a pathological condition (PTL 1). A method of predicting the onset of interstitial pneumonitis caused by interferon administration by measuring serum MUC-1/KL-6 levels (PTL 2), a method of examining prognosis in lung cancer patients by measuring KL-6 (PTL 3), and a method of detecting intraductal papillary mucinous carcinoma or pancreatic cancer by measuring KL-6 in pancreatic juice (PTL 4) have been disclosed. In recent years, the need has increased for KL-6 measurement for the diagnosis and determination of therapeutic strategies for interstitial pneumonitis including drug-induced interstitial pneumonitis, collagen disorder-induced interstitial pneumonitis, etc., diagnosis of patients with cancers of lung, pancreas, etc., and diagnosis and determination of therapeutic strategies for interstitial pneumonitis in patients treated with antibody preparation for rheumatoid arthritis, Crohn's disease, generalized juvenile idiopathic arthritis, Castleman's disease, etc.

In patent literature 1-4, enzyme-linked immunosorbent assay (hereinafter, ELISA method) has been used for KL-6 measurement. Although ELISA is a reliable method, latex immunoagglutination assay is superior for rapid, easy, and cheap testing of a large number of samples and is widely used as a clinical reagent for measuring trace components.

However, when a sample containing the rheumatoid factor is tested by an immunological measurement method such as ELISA or latex immunoagglutination, the occurrence of a nonspecific reaction owing to interference from the rheumatoid factor depending on the sample, is a known problem (NPL 2). In addition, the occurrence of a nonspecific reaction due to interference from heterophile antibodies (anti-mouse immunoglobulin antibody: HAMA etc. and anti-goat immunoglobulin antibody: HAGA etc.) is a known problem.

A method that removes the Fc portion from the antibody bound to the latex, a method that uses an antibody that binds to the rheumatoid factor (PTL 5), and other similar methods are known to inhibit interference from the rheumatoid factor in the latex immunoagglutination assay.

However, the present inventors have found samples in which the occurrence of nonspecific reactions could not be adequately inhibited even by the abovementioned methods.

PRIOR ART LITERATURE

Patent Literature

[Patent Literature 1] Japanese Published Examined Application No. 1995-31207

[Patent Literature 2] Japanese Published Unexamined Application No. 2005-121441

[Patent Literature 3] Japanese Patent Publication No. 4083855

[Patent Literature 4] Japanese Published Unexamined Application No. 2006-308576

[Patent Literature 5] Japanese Published Unexamined Application No. 1995-12818

Non-Patent Literature

[Non-Patent Literature 1] New serum indicator of interstitial pneumonitis activity. Sialylated carbohydrate antigen KL-6. Kohno N, Kyoizumi S, Awaya Y, Fukuhara H, Yamakido M, Akiyama M. Chest. 1989 July; 96 (1):68-73.

[Non-Patent Literature 2] Interference by rheumatoid factor with the detection of C-reactive protein by the latex agglutination method. Deyo R A, Pope R M, Persellin R H. J Rheumatol. 1980 May-June; 7 (3):279-87.

SUMMARY OF INVENTION

Problems to be Solved by the Invention

The present invention aims to provide an assay reagent and an assay for accurately measuring KL-6, in particular, an assay reagent and an assay for accurately measuring KL-6 in samples containing the rheumatoid factor and/or other nonspecific substances.

Means for Solving the Problem

Extensive studies by the present inventors indicated that KL-6 in samples containing the rheumatoid factor and/or other nonspecific substances can be accurately measured using an immunoassay reagent comprising a solution at pH 4.0 to 5.5 containing the rheumatoid factor interference inhibitor and an insoluble carrier on which anti-KL-6 antibodies are immobilized. This led to the completion of the present invention. More specifically, this invention has the following configuration.

(1) A KL-6 immunoassay reagent comprising a solution (pH 4.0 to 5.5) containing a rheumatoid factor interference inhibitor and a solution containing an insoluble carrier on which an anti-KL-6 antibody is immobilized.

(2) The immunoassay reagent of (1) above, wherein the insoluble carrier is a latex particle.

(3) A KL-6 immunoassay comprising measuring the change in absorbance accompanying agglutination of an insoluble carrier due to the immune reaction between KL-6 in a sample and an anti-KL-6 antibody immobilized on the insoluble carrier in a solution at pH 4.0 to 5.5, using the sample, a rheumatoid factor interference inhibitor, and an insoluble carrier on which an anti-KL-6 antibody is immobilized.

(4) A KL-6 immunoassay in which a solution at pH 4.0 to 5.5 containing a rheumatoid factor interference inhibitor and an insoluble carrier on which an anti-KL-6 antibody is immobilized is added to a sample and the change in absorbance accompanying the agglutination of the insoluble carrier due to the immune reaction between KL-6 in the sample and the anti-KL-6 antibody immobilized on the insoluble carrier is measured.

(5) The immunoassay of (3) or (4) above, wherein the insoluble carrier is a latex particle.

There are no particular restrictions on the rheumatoid factor interference inhibitor used in the present invention provided it inhibits rheumatoid factor interference in the immunoassay, and HBR (Scantibodies Lab) and animal-derived immunoglobulins that react with rheumatoid factor such as IgM, IgG, and IgA may be mentioned as examples.

As described above, the animal-derived immunoglobulins may be polyclonal or monoclonal antibodies.

The amount of the above mentioned rheumatoid factor interference inhibitor used is preferably 10 to 200 μg/mL.

Buffer solutions at pH 4.0 to 5.5, such as citric acid, acetic acid, glycine, and Good's buffers to which the rheumatoid factor interference inhibitor added, may be mentioned as the solution at pH 4.0 to 5.5 containing the rheumatoid factor interference inhibitor used in the present invention, and the concentration of the above mentioned buffer solution is preferably 5 to 200 mM.

As described in Patent Literature 1, the anti-KL-6 antibody used in the present invention can be prepared according to the conventional method of monoclonal antibody production after immunizing mice with the pulmonary adenocarcinoma-derived cell line VMRC-LCR as the antigen (Derivation of specific antibody-producing tissue culture and tumor lines by cell fusion. Kohler G, Milstein C. Eur J Immunol. 1976 July; 6 (7):511-9).

Organic polymer powders, inorganic powders, microorganisms, hematocytes, and cell debris may be mentioned as examples of the insoluble carrier used in the present invention.

Natural polymer powders such as insoluble agarose, cellulose, and insoluble dextran and synthetic polymer powders such as polystyrene, styrene-styrene sulfonate copolymers, acrylonitrile-butadiene-styrene copolymers, vinyl chloride-acrylate ester copolymers, and vinyl acetate-acrylic ester copolymers may be mentioned as examples of the above mentioned organic polymer powders, in particular, latex in which a synthetic polymer powder has been suspended uniformly is desirable.

Metal fragments such as gold, titanium, iron and nickel; silica; alumina and carbon powder may be mentioned as examples of the above mentioned inorganic powders.

While the average particle diameter of the above mentioned insoluble carrier depends on the assay and measuring device, particles with diameter from 0.05 to 1.0 μm are normally used.

Chemical or physical binding may be mentioned as the example of methods of immobilizing anti-KL-6 antibodies on the above mentioned insoluble carrier.

The above mentioned insoluble carrier on which anti-KL-6 antibodies are immobilized is normally present in a solution, and Tris, glycine, and Good's buffers may be mentioned as examples of the solutions used.

Physiologically (biological) derived body fluids may be mentioned as the "analytes" that are the major targets of measurement in the assay of the present invention. Blood, serum, plasma, urine, saliva, sputum, tears, ear discharge, or prostatic fluid may be specifically mentioned, but samples may not be limited to these.

Latex agglutination and hemagglutination reactions are examples of measurement systems used for measurement of antibody-antigen reactions using the above mentioned reagent. Methods whereby the degree of agglutination is optically examined may be employed as the method of measuring agglutination caused by the above mentioned reactions.

In particular, in the method of optical examination, scattered light intensity, absorbance, or transmitted light intensity accompanying agglutination of the insoluble carrier caused by an immunoreaction between KL-6 in the sample and anti-KL-6 antibodies immobilized on the insoluble carrier are measured after mixing the solution at pH 4.0 to 5.5, containing the above mentioned rheumatoid factor interference inhibitor, and sample with the solution of the above mentioned insoluble carrier on which anti-KL-6 antibodies are immobilized. Here the pH of the above mentioned mixture is preferably in the range of 4.0 to 5.5. A measuring wavelength of 300 to 1000 nm may be used, and the assay measures increase or decrease in scattered light intensity, absorbance, or transmitted light intensity according to the particle diameter, concentration, and reaction time of the insoluble carrier used, based on the knowledge of one skilled in the art.

In order to perform an immunoassay of the present invention, the immunoreaction between KL-6 in the sample and anti-KL-6 antibodies immobilized on the insoluble carrier should be performed under conditions in which the sample, rheumatoid factor interference inhibitor, and insoluble carrier on which anti-KL-6 antibodies are immobilized are present in a solution at pH 4.0 to 5.5.

Preferably 5 to 200 mM citric acid, acetic acid, glycine, and Good's buffer may be mentioned as examples of the above mentioned solution at pH 4.0 to 5.5.

Effect of the Invention

According to the present invention, in an immunoassay using an agglutination reaction of an insoluble carrier such as the latex immunoagglutination assay, numerous samples can be rapidly, readily, cheaply, and accurately tested, even when there are concerns about the occurrence or increase of non-specific reactions attributable to the rheumatoid factor or heterophile antibodies, nonspecific reactions where interference is not inhibited by antibodies binding to the rheumatoid factor or various animal-derived antibodies, nonspecific reactions attributable to something other than the rheumatoid factor or heterophile antibodies, nonspecific reactions due to the use of antibody preparations, etc.

DESCRIPTION OF EMBODIMENTS

Materials and Methods

<Anti-KL-6 Antibody>

The antibody obtained by the method described in Patent Literature 1 (particularly in the first example) was used as the anti-KL-6 antibody. The method of antibody production described in Patent Literature 1 is as follows:

1) Immunization

Eight-week-old female BALB/c mice were immunized subcutaneously with $5\times10^6$ cells derived from a pulmonary adenocarcinoma cell line (hereinafter VMRC-LCR), and subsequently, the mice were intraperitoneally injected with $8\times10^6$ cells twice at an interval of 2 weeks.

2) Cell Fusion

Three days after final immunization, the spleen was removed and passed through a stainless mesh to prepare a cell suspension. Spleen cells ($8.4\times10^7$) were mixed with P3-NSI-Ag4/1 (NSI) 8-azaguanine-resistant myeloma cells ($4.2\times10^7$) and centrifuged. Next, 1 mL of 45% polyethylene glycol (average molecular weight 6000) was added to the precipitate, and the mixture was stirred gently for 2 min. After washing, the mixture was suspended in RPMI medium containing 10% fetal calf serum (complete RPMI medium), and $10^6$ cells at 0.1 mL per well were added to a 96-well microculture plate. After 24 h, 0.1 mL of complete RPMI medium containing 100 of hypoxanthine, 0.4 μM of aminopterin, and 16 μM of thymidine (HAT medium) was added. On the second, third, fifth, seventh, and tenth day after the start of culture, 0.1 mL of culture supernatant was discarded and an equal volume (0.1 mL) of HAT medium was added. Proliferation of hybridomas was observed in all wells after 12 days.

3) Selection of Hybridomas

Hybridomas producing antibodies to VMRC-LCR cells were selected by an enzyme immunoassay. The enzyme immunoassay was performed as follows:

VMRC-LCR cells were cultured in a 96-well microculture plate until confluence, fixed for 5 to 7 min in 0.25% glutaraldehyde, and washed five times. Next, 0.1 mL of hybridoma culture supernatant was added, and the mixture was allowed to react for 1 h at room temperature. After washing five times, 50 μL of the horseradish peroxidase-conjugated goat anti-mouse immunoglobulin was added as the secondary antibody and allowed to react for 1 h. After washing six to seven times, 100 μL of 50 mM citric acid buffer containing 1.1% hydrogen peroxide solution and 150 μg/mL 2,2'-azino-bis(3-ethylbenzthiazoline-6-sulfonic acid) (ABTS) was added, and the mixture was allowed to develop color for 10 min at room temperature. Next, 50 μL of 10% oxalic acid was added to stop the reaction. The absorbance at 405 nm was measured by a microplate spectrophotometer, and hybridomas with absorbance of 0.02 or more were selected.

The selected hybridomas were transferred to a 24-well culture plate in which BALB/c mouse thymocytes (feeder cells) had been attached, and were cultured with complete RPMI medium containing 100 μM hypoxanthine and 16 μM thymidine (HT medium). After reaching confluence, hybridomas producing antibodies against VMRC-LCR cells were again selected by an enzyme immunoassay.

Next, the selected hybridomas were cloned by the limiting dilution method. In brief, cells were diluted to 50 or 10 cells/mL, added to a 96-well microculture plate containing feeder cells at 0.1 mL per well, and cultured for 2 weeks with HT medium. Clones from wells with a single hybridoma colony were selected. These clones were reacted with VMRC-LCR cells by an enzyme immunoassay, and hybridoma clones that secreted antibodies showing no reaction to normal human pulmonary fibroblasts were selected.

Clones that reacted with human pulmonary fibroblasts were selected from among these clones by immunoperoxidase staining of frozen sections. Specifically, human pulmonary carcinomas and carcinomas of other organs as well as normal tissue were obtained by surgical procedures and 4-μm frozen sections were prepared. After acetone fixation, the hybridoma clone culture supernatant was added, and the mixture was allowed to react for 30 min at room temperature. After thorough washing, the mixture was allowed to react with the biotinylated anti-mouse IgG antibody (reacting to γ chain, λ chain, and κ chain) for 30 min at room temperature. After further washing, avidin-biotinylated horseradish peroxidase was added, and the mixture was allowed to react for 1 h at room temperature. After thorough washing, 50 mM Tris-HCl buffer containing 0.5 mg/mL diaminobenzidine (as substrate) and 0.01% hydrogen peroxide (pH 7.0) was added, and the mixture was allowed to develop color.

In this manner, a hybridoma producing monoclonal antibodies that reacted with alveolar epithelium; bronchiolar epithelium; bronchial gland serous cells; thyroid follicular cells; esophageal epithelium; cardiac gland cells; pancreatic duct epithelium; tubular epithelium; urinary bladder transitional epithelium; endometrium; pulmonary adenocarcinoma; pulmonary squamous cell carcinoma; pulmonary small cell carcinoma; adenocarcinoma of the stomach, duodenal papilla, bile duct, pancreas, colon, rectum, thyroid, and mammary gland; and esophageal squamous cell carcinoma, but not with bronchial epithelium; superficial gastric mucosal cells; pyloric gland; duodenal epithelium; colonic epithelium; rectal epithelium; hepatocytes; pancreatic exocrine cells; pancreatic endocrine cells; renal glomerular cells; cervical squamous cell; dermal epithelium; cervical squamous cell carcinoma; and hepatocellular carcinoma was obtained. This hybridoma was named a KL-6 cell and the monoclonal antibody it produced was named anti-KL-6 antibody.

4) Monoclonal Antibody Production

In Vivo Transplantation

BALB/c mice to be transplanted with the hybridoma were injected intraperitoneally with 0.5 mL of 2,6,10,14-tetramethylpentadecane in advance (5 to 10 days before), and $5\times10^6$ hybridoma cells were intraperitoneally transplanted. After 3 weeks, intraperitoneal hybridoma tumors formed and the abdomen enlarged in the transplanted mouse.

As a result, a high concentration of monoclonal antibody was generated in the ascites fluid and blood serum, and these fluids were collected.

<Preparation of Latex Particles>

In brief, 1100 g of distilled water, 200 g of styrene, 0.2 g sodium styrene sulfonate, and an aqueous solution of 1.5 g of potassium persulfate dissolved in 50 g of distilled water were mixed in a 2-L glass reaction vessel fitted with a stirrer, reflux condenser, temperature detector, nitrogen inlet, and jacket. The atmosphere in the vessel was replaced with nitrogen gas, and the mixture was polymerized for 48 h at 70° C. with stirring.

After polymerization, the above mentioned solution was filtered through a filter paper and latex particles were recovered. The diameter of the obtained latex particles was measured by image analysis of at least 100 particles. Photographs for image analysis of the latex particles were taken at a magnification of 10,000× using a transmission electron microscope (JEM-1010, JEOL). The average diameter was 0.2 μm.

EXAMPLES

Example 1

Preparation of a Solution Containing Anti-KL-6 Antibody-Immobilized Latex Particle (a Solution Containing Latex Particles on Which Anti-KL-6 Antibodies are Immobilized; Hereinafter Referred to as Reagent 2)

An anti-KL-6 antibody solution (5 mM Tris-HCl, pH 8.0) adjusted to 0.7 mg/mL was added to an equal amount of solution containing 1.0% latex particles having an average particle diameter of 0.2 μm (5 mM Tris-HCl, pH 8.0). After stirring for 2 h at 4° C., an equal amount of 2.0% BSA solution (5 mM Tris-HCl, pH 8.0) was added, and the mixture was stirred for 1 h at 4° C. After centrifugation, the supernatant was discarded, and the precipitate was resuspended in 5 mM Tris-HCl, pH 8.0. This mixture was diluted with 5 mM Tris-HCl, pH 8.0 such that the absorbance at a wavelength of 600 nm was 4.5 Abs. This solution was used as Reagent 2.

Preparation of a solution containing the rheumatoid factor interference inhibitor (hereinafter, Reagent 1).

Specifically, 30 mM citrate buffer (pH 4.0) containing 1000 mM sodium chloride, 1.0% BSA, and 50 μg/mL HBR (Scantibodies Lab, 3KC533) was prepared and used as Reagent 1.

(Sample)

The concentration of the rheumatoid factor in samples from patients with rheumatism were measured by the N-assay Nittobo TIA RF (Nittobo Medical Co., Ltd.) and the concentration of KL-6 was measured using Picolumi (registered trademark) KL-6 (Sanko Junyaku Co., Ltd.); each was measured according to the respective product documentation and manufacturer's instructions. The measured KL-6 value was expressed as 100% and was compared with the measured value according to the immunoassay of the present invention.

(Assay of KL-6 Concentration)

Reagent 1 and Reagent 2 were mixed, and the concentration of KL-6 in the sample containing the rheumatoid factor was measured using a Hitachi 7170 automated analyzer. Specifically, 150 μL of Reagent 1 was added to 2.5 μL of sample and after incubating for 5 min at 37° C., 50 μL of Reagent 2 was added, and the mixture was stirred. Changes in absorbance associated with agglutination were measured over the next 5 min at a main wavelength of 570 nm and a sub-wavelength of 800 nm. The concentration of KL-6 was calculated by applying the change in absorbance to a calibration curve obtained by measurement of a standard substance of known concentration.

(pH Assay of the Mixture)

After mixing the sample, Reagent 1, and Reagent 2 in the same ratio as in the above mentioned assay of KL-6, pH was measured using a Castany LAB F-21 pH meter (Horiba Ltd.).

Examples 2 to 4

Instead of 30 mM citrate buffer (pH 4.0) in Reagent 1 of Example 1, 30 mM citrate buffers at pH 4.5 (Example 2), pH 5.0 (Example 3), and pH 5.5 (Example 4) were used. Measurements were performed using the same reagents and the same assay as Example 1.

Comparative Examples 1 to 6

Measurements were performed using the same reagents and the same assay as Example 1 except that 30 mM glycine buffer at pH 3.5 (Comparative Example 1) and 30 mM phosphate buffers at pH 6.0 (Comparative Example 2), 6.5 (Comparative Example 3), 7.0 (Comparative Example 4), 7.5 (Comparative Example 5), and 8.0 (Comparative Example 6) were used instead of 30 mM citrate buffer (pH 4.0) in Reagent 1 of Example 1.

Results and Discussion

The effectiveness of nonspecific reaction inhibition when the pH of Reagent 1 was varied was investigated for a sample containing a high concentration of the rheumatoid factor (elevated rheumatoid factor sample). Results of measurements of Reagent 1 at pH 3.5 to 8.0 for elevated rheumatoid factor samples A and B and normal sample C (Examples 1 to 4, Comparative Examples 1 to 6) are shown in Table 1.

Considering the KL-6 concentration measured by Picolumi (registered trademark) KL-6 to be 100%, nonspecific reactions were believed to occur when the KL-6 values measured by the assay of the present invention were less than 85% or more than 115%. If the values were within the range of 85% to 115%, the method was considered to have sufficient accuracy, and the effectiveness of nonspecific reaction inhibition was confirmed.

Using the rheumatoid factor interference inhibitor and the pH range of the prior art (pH 6.0 to 8.0), measured values for the elevated rheumatoid factor sample B were within the range of 85% to 115% of the values measured by Picolumi (registered trademark) KL-6. On the other hand, measured values for the high rheumatoid factor sample A, exceeded 115% of the values measured by Picolumi (registered trademark) KL-6 in the pH range of the prior art (comparative examples 2 to 6), and a nonspecific reaction was observed, which could not be sufficiently inhibited even by the rheumatoid factor interference inhibitor.

Surprisingly, after changing the pH of Reagent 1 to the range from 4.0 to 5.5, measured values for both the elevated rheumatoid factor samples A and B were within the range of 85% to 115% of values measured by Picolumi (registered trademark) KL-6 and nonspecific reactions were inhibited (Examples 1 to 4). This result showed that the rheumatoid factor and non-rheumatoid factor nonspecific reactions were inhibited by the present invention, and measured values were accurate. Since no pH- or buffer-dependent variation was observed in measured values for sample C, it was confirmed that varying pH or changing buffers does not affect the measured values of KL-6.

The results of pH measurement when the sample, Reagent 1, and Reagent 2 were mixed in the same ratio as in the above mentioned KL-6 concentration assay are shown in Table 2.

TABLE 1

| Sample dilution solution pH | | | | | | | Glycine | Phosphoric acid | | | | |
|---|---|---|---|---|---|---|---|---|---|---|---|---|
| | | KL-6 | Citric acid | | | | 3.5 | 6.0 | 6.5 | 7.0 | 7.5 | 8.0 |
| | RF conc. (IU/mL) | conc.* (U/mL) | 4.0 Ex. 1 | 4.5 Ex. 2 | 5.0 Ex. 3 | 5.5 Ex. 4 | Comp. Ex. 1 | Comp. Ex. 2 | Comp. Ex. 3 | Comp. Ex. 4 | Comp. Ex. 5 | Comp. Ex. 6 |
| Sample A | 1019 | 553 | 109.7% | 111.3% | 111.6% | 111.6% | 120.4% | 146.5% | 143.0% | 137.8% | 135.9% | 123.8% |
| Sample B | 894 | 2880 | 109.6% | 112.8% | 114.5% | 112.1% | 114.3% | 113.0% | 112.1% | 114.1% | 114.5% | 114.9% |
| Sample C | 11 | 494 | 94.4% | 91.0% | 89.5% | 93.0% | 100.5% | 91.6% | 85.1% | 86.0% | 90.5% | 93.3% |

Glycine: Glycine buffer
Citric acid: Citrate buffer
Phosphoric acid: Phosphate buffer
RF: Rheumatoid factor
*Measurement by Picolumi (registered trademark) KL-6
Percentage in Examples and Comparative Examples is relative to a value of 100% of measurements by Picolumi (registered trademark) KL-6
Conc.: Concentration
Ex.: Example
Comp. Ex.: Comparative Example

TABLE 2

| | Citric acid | | | | Glycine | Phosphoric acid | | | | |
|---|---|---|---|---|---|---|---|---|---|---|
| | | | | | 3.5 | 6.0 | 6.5 | 7.0 | 7.5 | 8.0 |
| Sample dilution solution pH | 4.0 Ex. 1 | 4.5 Ex. 2 | 5.0 Ex. 3 | 5.5 Ex. 4 | Comp. Ex. 1 | Comp. Ex. 2 | Comp. Ex. 3 | Comp. Ex. 4 | Comp. Ex. 5 | Comp. Ex. 6 |
| Sample A | 4.0 | 4.5 | 5.0 | 5.5 | 3.5 | 6.0 | 6.5 | 7.0 | 7.5 | 8.0 |
| Sample B | 4.0 | 4.5 | 5.0 | 5.5 | 3.5 | 6.0 | 6.5 | 7.0 | 7.5 | 8.0 |
| Sample C | 4.0 | 4.5 | 5.0 | 5.5 | 3.5 | 6.0 | 6.5 | 7.0 | 7.5 | 8.0 |

Glycine: Glycine buffer
Citric acid: Citrate buffer
Phosphoric acid: Phosphate buffer
Ex.: Example
Comp. Ex.: Comparative Example As described above, the pH of Reagent 1 (pH 4.0 to 5.5), for which nonspecific reactions were not observed, was still 4.0 to 5.5 after mixing. (Examples 1 to 4). This suggested that the same effectiveness of inhibition of nonspecific reactions could be obtained by using a pH from 4.0 to 5.5 when measuring KL-6 concentration.

Examples 5 and 6 and Comparative Examples 7 to 10

Preparation of Reagent 1

Examples 5 and 6

30 mM citrate buffer (Example 5: pH 4.0, 4.5, 5.0, and 5.5) and 30 mM acetate buffer (Example 6: pH 4.0, 4.5, 5.0, and 5.5) containing 1000 mM sodium chloride, 1.0% BSA, and 50 μg/mL HBR (Scantibodies Lab, 3KC533) were prepared as solutions containing the rheumatoid factor interference inhibitor.

Comparative Example 7

In brief, 30 mM phosphate buffer (pH 6.0, 6.5, 7.0, 7.5, and 8.0), 30 mM glycine buffer (pH 3.5), and 30 mM citrate buffer (pH 4.0, 4.5, 5.0, 5.5, and 6.0) containing 1000 mM sodium chloride and 1.0% BSA were prepared as solutions not containing the rheumatoid factor interference inhibitor (without HBR).

Comparative Example 8

30 mM phosphate buffer (pH 6.0, 6.5, 7.0, 7.5, and 8.0), 30 mM glycine buffer (pH 3.5), and 30 mM citrate buffer (pH 6.0) containing 1000 mM sodium chloride, 1.0% BSA, and 50 μg/mL HBR (Scantibodies Lab, 3KC533) were prepared as solutions containing the rheumatoid factor interference inhibitor.

Comparative Example 9

30 mM phosphate buffer (pH 6.0, 6.5, 7.0, 7.5, and 8.0), 30 mM glycine buffer (pH 3.5), and 30 mM acetate buffer (pH 4.0, 4.5, 5.0, 5.5, and 6.0) containing 1000 mM sodium chloride and 1.0% BSA were prepared as solutions not containing the rheumatoid factor interference inhibitor.

Comparative Example 10

30 mM phosphate buffer (pH 6.0, 6.5, 7.0, 7.5, and 8.0), 30 mM glycine buffer (pH 3.5), and 30 mM acetate buffer (pH 6.0) containing 1000 mM sodium chloride, 1.0% BSA, and 50 μg/mL HBR (Scantibodies Lab, 3KC533) were prepared as solutions containing the rheumatoid factor interference inhibitor.

(Sample Measurement)

KL-6 concentrations were measured by the same assay as Example 1, using the buffer described above under Examples 5 and 6 and Comparative Examples 7 to 10 as the respective Reagent 1 and Reagent 2 described in Example 1 as Reagent 2.

Results and Discussion

Effectiveness of nonspecific reaction inhibition was investigated when the pH of solutions containing or not containing the rheumatoid factor interference inhibitor differed. The results are shown in Tables 3, 4, and 5. Samples were divided into groups a, b, and c as in the table on the basis of the behavior of each specimen under various conditions.

TABLE 3

Measured value at each pH in solutions not containing the rheumatoid factor interference inhibitor (Comparative Example 7)

| | | RF conc. | KL-6 conc.* | Citric acid | | | | Glycine | Citric acid |
|---|---|---|---|---|---|---|---|---|---|
| | | (IU/mL) | (U/mL) | 4.0 | 4.5 | 5.0 | 5.5 | 3.5 | 6.0 |
| Group a | Sample D | 100 | 211 | 131.9% | 116.5% | 116.0% | 115.3% | 138.3% | 133.9% |
| | Sample E | 1755 | 953 | 141.8% | 131.2% | 157.5% | 323.8% | 707.8% | 704.8% |

TABLE 3-continued

Measured value at each pH in solutions not containing the rheumatoid factor interference inhibitor (Comparative Example 7)

| | | | | | | | | | |
|---|---|---|---|---|---|---|---|---|---|
| Group b | Sample F | 371 | 284 | 145.3% | 116.5% | 123.9% | 127.2% | 126.1% | 271.1% |
| | Sample G | 376 | 301 | 123.2% | 199.5% | 253.2% | 326.8% | 217.4% | 461.8% |
| | Sample H | 18 | 752 | 212.3% | 153.9% | 134.6% | 134.5% | 131.1% | 137.9% |
| Group c | Sample I | 8 | 1327 | 108.9% | 99.5% | 94.3% | 96.1% | 92.2% | 92.0% |
| | Sample J | 144 | 708 | 102.9% | 102.9% | 99.7% | 105.2% | 107.8% | 105.9% |

| | | RF conc. | KL-6 conc.* | Phosphoric acid | | | | |
|---|---|---|---|---|---|---|---|---|
| | | (IU/mL) | (U/mL) | 6.0 | 6.5 | 7.0 | 7.5 | 8.0 |
| Group a | Sample D | 100 | 211 | 117.6% | 133.8% | 146.5% | 142.8% | 140.1% |
| | Sample E | 1755 | 953 | 875.3% | 659.9% | 499.6% | 542.2% | 605.4% |
| Group b | Sample F | 371 | 284 | 150.6% | 273.0% | 380.2% | 267.6% | 171.3% |
| | Sample G | 376 | 301 | 256.3% | 375.4% | 610.3% | 693.6% | 737.5% |
| | Sample H | 18 | 752 | 134.7% | 137.5% | 145.6% | 134.9% | 126.5% |
| Group c | Sample I | 8 | 1327 | 97.0% | 97.8% | 97.9% | 98.3% | 96.9% |
| | Sample J | 144 | 708 | 108.5% | 109.4% | 112.8% | 110.7% | 113.1% |

Glycine: Glycine buffer

Citric acid: Citrate buffer

Phosphoric acid: Phosphate buffer

RF: Rheumatoid factor

*Measurement by Picolumi (registered trademark) KL-6

Percentage is relative to a value of 100% of measurements by Picolumi (registered trademark) KL-6

Figures in gray shaded area: Values greater than ±15% of Picolumi (registered trademark) KL-6

4.0, 4.5, 5.0, 5.5, 3.5, 6.0, 6.5, 7.0, and 8.0 under the names of the buffers represent the pH of the sample dilution solutions Conc.: Concentration

TABLE 4

Measured value at each pH in solutions containing the rheumatoid factor interference inhibitor [Example 5 (pH 4.0-5.5) and Comparative Example 8 (pH 3.5, 6.0-8.0)]

| | | RF conc. | KL-6 conc.* | Citric acid | | | | Glycine | Citric acid |
|---|---|---|---|---|---|---|---|---|---|
| | | (IU/mL) | (U/mL) | 4.0 | 4.5 | 5.0 | 5.5 | 3.5 | 6.0 |
| Group a | Sample D | 100 | 211 | 92.0% | 108.8% | 110.9% | 110.3% | 128.5% | 123.8% |
| | Sample E | 1755 | 953 | 105.2% | 109.3% | 109.7% | 112.2% | 140.5% | 132.4% |
| Group b | Sample F | 371 | 284 | 96.7% | 98.0% | 99.5% | 103.1% | 102.7% | 104.6% |
| | Sample G | 376 | 301 | 94.9% | 100.5% | 100.2% | 97.5% | 101.6% | 101.4% |
| | Sample H | 18 | 752 | 96.8% | 97.0% | 101.8% | 103.9% | 102.7% | 101.3% |
| Group c | Sample I | 8 | 1327 | 110.7% | 98.9% | 97.3% | 96.2% | 97.2% | 92.3% |
| | Sample J | 144 | 708 | 101.2% | 103.7% | 99.1% | 99.5% | 104.0% | 98.0% |

TABLE 4-continued

Measured value at each pH in solutions containing the rheumatoid factor interference inhibitor [Example 5 (pH 4.0-5.5) and Comparative Example 8 (pH 3.5, 6.0-8.0)]

| | | RF conc. | KL-6 conc.* | Phosphoric acid | | | | |
|---|---|---|---|---|---|---|---|---|
| | | (IU/mL) | (U/mL) | 6.0 | 6.5 | 7.0 | 7.5 | 8.0 |
| Group a | Sample D | 100 | 211 | 115.6% | 125.2% | 130.1% | 131.6% | 127.6% |
| | Sample E | 1755 | 953 | 123.2% | 130.3% | 160.5% | 175.6% | 180.7% |
| Group b | Sample F | 371 | 284 | 101.5% | 96.9% | 99.0% | 97.4% | 97.4% |
| | Sample G | 376 | 301 | 97.5% | 94.6% | 98.9% | 97.2% | 96.0% |
| | Sample H | 18 | 752 | 105.3% | 100.4% | 101.3% | 101.1% | 99.5% |
| Group c | Sample I | 8 | 1327 | 97.0% | 98.9% | 98.7% | 98.3% | 97.3% |
| | Sample J | 144 | 708 | 101.9% | 103.7% | 102.7% | 101.4% | 100.9% |

Glycine: Glycine buffer
Citric acid: Citrate buffer
Phosphoric acid: Phosphate buffer
RF: Rheumatoid factor
*Measurement by Picolumi (registered trademark) KL-6
Percentage is relative to a value of 100% of measurements by Picolumi (registered trademark) KL-6
Figures in gray shaded area: Values greater than ±15% of Picolumi (registered trademark) KL-6
4.0, 4.5, 5.0, 5.5, 3.5, 6.0, 6.5, 7.0, and 8.0 under the names of the buffers represent the pH of the sample dilution solutions
Conc.: Concentration

TABLE 5

Measured value at each pH in solutions not containing and containing the rheumatoid factor interference inhibitor

| | | RF conc. | KL-6 conc.* | Acetic acid | | | | Glycine | Acetic acid |
|---|---|---|---|---|---|---|---|---|---|
| | | (IU/mL) | (U/mL) | 4.0 | 4.5 | 5.0 | 5.5 | 3.5 | 6.0 |
| (1) Solutions not containing the rheumatoid factor interference inhibitor (Comparative Example 9) | | | | | | | | | |
| Group a | Sample D | 100 | 211 | 122.1% | 116.1% | 119.3% | 128.2% | 138.3% | 148.1% |
| | Sample E | 1755 | 953 | 149.1% | 152.0% | 179.1% | 911.5% | 707.8% | 631.0% |
| Group b | Sample F | 371 | 284 | 127.4% | 117.5% | 124.2% | 150.3% | 126.1% | 325.7% |
| | Sample G | 376 | 301 | 163.9% | 207.8% | 291.8% | 412.7% | 217.4% | 468.8% |
| | Sample H | 18 | 752 | 168.8% | 139.5% | 134.2% | 135.4% | 131.1% | 142.7% |
| Group c | Sample I | 8 | 1327 | 94.7% | 91.2% | 91.4% | 91.2% | 92.2% | 93.7% |
| | Sample J | 144 | 708 | 96.0% | 98.8% | 98.8% | 103.8% | 107.8% | 108.8% |
| (2) Solutions containing the rheumatoid factor interference inhibitor [Example 6 (pH 4.0-5.5) and Comparative Example 10 (pH 3.5 and 6.0-8.0)] | | | | | | | | | |
| Group a | Sample D | 100 | 211 | 104.9% | 105.7% | 102.6% | 113.0% | 128.5% | 126.4% |
| | Sample E | 1755 | 953 | 111.9% | 104.7% | 112.3% | 114.9% | 140.5% | 142.4% |
| Group b | Sample F | 371 | 284 | 91.2% | 98.2% | 102.1% | 101.0% | 102.7% | 98.5% |
| | Sample G | 376 | 301 | 105.1% | 97.2% | 104.9% | 105.8% | 101.6% | 102.8% |
| | Sample H | 18 | 752 | 86.7% | 96.3% | 97.6% | 101.8% | 102.7% | 99.9% |

TABLE 5-continued

| Measured value at each pH in solutions not containing and containing the rheumatoid factor interference inhibitor | | | | | | | | | |
|---|---|---|---|---|---|---|---|---|---|
| Group c | Sample I | 8 | 1327 | 92.3% | 91.7% | 90.2% | 92.7% | 97.2% | 94.0% |
| | Sample J | 144 | 708 | 93.8% | 94.2% | 95.7% | 96.9% | 104.0% | 101.3% |

| | | RF conc. (IU/mL) | KL-6 conc.* (U/mL) | Phosphoric acid 6.0 | 6.5 | 7.0 | 7.5 | 8.0 |
|---|---|---|---|---|---|---|---|---|
| (1) Solutions not containing the rheumatoid factor interference inhibitor (Comparative Example 9) | | | | | | | | |
| Group a | Sample D | 100 | 211 | 117.6% | 133.8% | 146.5% | 142.8% | 140.1% |
| | Sample E | 1755 | 953 | 875.3% | 659.9% | 499.6% | 542.2% | 605.4% |
| Group b | Sample F | 371 | 284 | 150.6% | 273.0% | 380.2% | 267.6% | 171.3% |
| | Sample G | 376 | 301 | 256.3% | 375.4% | 610.3% | 693.6% | 737.5% |
| | Sample H | 18 | 752 | 134.7% | 137.5% | 145.6% | 134.9% | 126.5% |
| Group c | Sample I | 8 | 1327 | 97.0% | 97.8% | 97.9% | 98.3% | 96.9% |
| | Sample J | 144 | 708 | 108.5% | 109.4% | 112.8% | 110.7% | 113.1% |
| (2) Solutions containing the rheumatoid factor interference inhibitor [Example 6 (pH 4.0-5.5) and Comparative Example 10 (pH 3.5 and 6.0-8.0)] | | | | | | | | |
| Group a | Sample D | 100 | 211 | 115.6% | 125.2% | 130.1% | 131.6% | 127.6% |
| | Sample E | 1755 | 953 | 123.2% | 130.3% | 160.5% | 175.6% | 180.7% |
| Group b | Sample F | 371 | 284 | 101.5% | 96.9% | 99.0% | 97.4% | 97.4% |
| | Sample G | 376 | 301 | 97.5% | 94.6% | 98.9% | 97.2% | 96.0% |
| | Sample H | 18 | 752 | 105.3% | 100.4% | 101.3% | 101.1% | 99.5% |
| Group c | Sample I | 8 | 1327 | 97.0% | 98.9% | 98.7% | 98.3% | 97.3% |
| | Sample J | 144 | 708 | 101.9% | 103.7% | 102.7% | 101.4% | 100.9% |

Glycine: Glycine buffer
Citric acid: Citrate buffer
Phosphoric acid: Phosphate buffer
RF: Rheumatoid factor
*Measurement by Picolumi (registered trademark) KL-6
Percentage is relative to a value of 100% of measurements by Picolumi (registered trademark) KL-6
Figures in gray shaded area: Values greater than ±15% of Picolumi (registered trademark) KL-6
4.0, 4.5, 5.0, 5.5, 3.5, 6.0, 6.5, 7.0, and 8.0 under the names of the buffers represent the pH of the sample dilution solutions
Conc.: Concentration Excellent results of ±15% of values measured by Picolumi (registered trademark) KL-6 were obtained from group c in Tables 3 and 4 at every pH, regardless of the presence of the rheumatoid factor interference inhibitor suggesting that the rheumatoid factor interference inhibitor itself had no adverse effect on measured values.

On the other hand, the existence of specimens that exceed 115% of values measured by Picolumi (registered trademark) KL-6 and for which nonspecific reactions occur when measured using solutions not containing the rheumatoid factor interference inhibitor, such as specimens included in groups a and b in Table 3, was confirmed.

Excellent results were obtained for specimens from group b in Table 4 when the rheumatoid factor interference inhibitor was added, regardless of pH, and the rheumatoid factor interference inhibitor was confirmed to inhibit nonspecific reactions. On the other hand, at pH 3.5 and between pH 6.0 and 8.0, no nonspecific reaction-inhibiting effect was observed for specimens from group a in Table 4, even when the rheumatoid factor interference inhibitor was added; however, between pH 4.0 and 5.5, a strong nonspecific reaction-inhibiting effect was observed.

Even when buffer was changed from citric acid (tricarboxylic acid) to acetic acid (monocarboxylic acid) having pH 4.0 to 6.0, while there were specimens that exceeded 115% of values measured by Picolumi (registered trademark) KL-6 and for which nonspecific reactions occurred with solutions not containing the rheumatoid factor interference inhibitor [Table 5 (1)], the same nonspecific reaction-inhibiting effect as in the case of citrate buffer was observed with solutions that did include the rheumatoid factor interference inhibitor between pH 4.0 and 5.5 [Table 5 (2)]. On the other hand, in group a in Tables 3 to 5, no nonspecific reaction inhibiting-effect was observed at pH 6.0 using either citrate or acetate buffer, suggesting that using the rheumatoid factor interference inhibitor, and adjusting the pH of the sample diluted solution to between 4.0 and 5.5 when measuring KL-6 would inhibit nonspecific reactions most effectively, regardless of the type of buffer.

INDUSTRIAL APPLICABILITY

The present invention provides a method to measure KL-6 to assist the diagnosis and determination of therapeutic strategies for interstitial pneumonitis and an assay reagent or reagent kit for the implementation of the above mentioned method. The present invention is useful for the diagnosis and determination of therapeutic strategies for interstitial pneumonitis including drug-induced interstitial pneumonitis and collagen disorder-originating interstitial pneumonitis, diagnosis of patients with cancers such as lung cancer and pancreatic cancer, and for purposes such as diagnosis and determination of therapeutic strategies for interstitial pneumonitis in patients treated with antibody preparation for rheumatoid arthritis, Crohn's disease, generalized juvenile idiopathic arthritis, and Castleman's disease. Since the present invention is protected as necessary as a reagent, reagent kit, and a use of these in manufacturing, it has industrial applicability and is not excluded from patentability.

The invention claimed is:

1. A KL-6 immunoassay reagent kit; comprising:

a first solution at a pH of 4.0 to pH 5.5 containing a rheumatoid factor interference inhibitor; and a second solution containing an insoluble carrier on which an anti-KL-6 antibody is immobilized.

2. The immunoassay reagent kit according to claim 1 wherein the insoluble carrier is a latex particle.

3. A KL-6 immunoassay comprising:

providing a sample, a rheumatoid factor interference inhibitor, and an insoluble carrier on which an anti-KL-6 antibody is immobilized; and measuring the change in absorbance accompanying the agglutination of the insoluble carrier due to the immune reaction between KL-6 in the sample and an anti-KL-6 antibody immobilized on the insoluble carrier in a solution at a pH of 4.0 to pH 5.5.

4. A KL-6 immunoassay comprising:

adding to a sample a solution at a pH of 4.0 to pH 5.5 containing a rheumatoid factor interference inhibitor and a solution of solution containing an insoluble carrier on which an anti-KL-6 antibody is immobilized; and measuring the change in absorbance accompanying the agglutination of the insoluble carrier due to the immune reaction between KL-6 in the sample and the anti-KL-6 antibody immobilized on the insoluble carrier.

5. The immunoassay according to claim 3 or 4 wherein the insoluble carrier is a latex particle.

6. A KL-6 immunoassay comprising:

adding to a sample the first solution according to claim 1 and the second solution according to claim 1; and measuring the change in absorbance accompanying the agglutination of the insoluble carrier due to the immune reaction between KL-6 in the sample and the anti-KL-6 antibody immobilized on the insoluble carrier.

7. The immunoassay according to claim 3 or 6 wherein the insoluble carrier is a latex particle.

* * * * *